(12) United States Patent
Majeed et al.

(10) Patent No.: US 8,247,003 B2
(45) Date of Patent: Aug. 21, 2012

(54) PROTECTIVE COMPOSITIONS FOR DERMAL PAPILLA CELLS

(76) Inventors: Muhammed Majeed, Edison, NJ (US); Kalyanam Nagabhushanam, East Windsor, NJ (US); Beena Bhat, Bangalore (IN); Geetha Kanhangad-Gangadharan, Bangalore (IN); Susmitha Anand-Tathapudi, Bangalore (IN); Pritee Paliwal, Bangalore (IN)

( * ) Notice: Subject to any disclaimer, the term of this patent is extended or adjusted under 35 U.S.C. 154(b) by 252 days.

(21) Appl. No.: 12/537,843

(22) Filed: Aug. 7, 2009

(65) Prior Publication Data

US 2011/0033565 A1 Feb. 10, 2011

(51) Int. Cl.
*A61K 36/00* (2006.01)
(52) U.S. Cl. ........................................................ 424/725
(58) Field of Classification Search .................. None
See application file for complete search history.

(56) References Cited

U.S. PATENT DOCUMENTS

2004/0067264 A1* 4/2004 Majeed et al. ................ 424/727

OTHER PUBLICATIONS

Natural Remedies (see website article from www.natualremedy.com/nr/emblica-officinalis-amla.htm, pp. 1-3, copyrighted 2007-2009).*
Majeed et al. (Asocorbic Acid and Tannins from Emblica officinalis, Journal of Agricultural and Food Chemistry 2009,57, 220- 225, publication date Dec. 8, 2008).*

* cited by examiner

*Primary Examiner* — Melenie McCormick
*Assistant Examiner* — Randall Winston

(57) ABSTRACT

Disclosed are novel protective compositions for dermal papilla cells. In an embodiment the protective compositions of the present invention comprise 0.25% w/w or above of compositions comprising at least 10% w/w and above of 1-O-galloyl-β-D-glucose (β-glucogallin). In an embodiment, the said protective composition additionally comprises 50% to greater than 50% gallates including mucic acid 1,4-lactone 5-O-gallate, mucic acid 2-O-gallate, mucic acid 6-Methyl ester 2-O-gallate, mucic acid 1-Methyl ester 2-O-gallate and ellagic acid. In another embodiment the invention also encompasses synergistic protective compositions comprising the said protective compositions and 0.5% concentrate of liquid endosperm of *Cocos nucifera*, for dermal papilla directed towards helping the dermal papilla cells to form sufficient numbers and to retain a healthy morphology conducive for hair growth.

3 Claims, 5 Drawing Sheets

Increasing dosages of UV (J cm$^{-2}$)

Row I: Untreated cells 0.0072    0.0216    0.216    0.432

0.0072    0.0216    0.216    0.432

Row II: PC-I treated cells

FIG. II
Increasing dosages of UV (J cm$^{-2}$)
Row I: Untreated cells
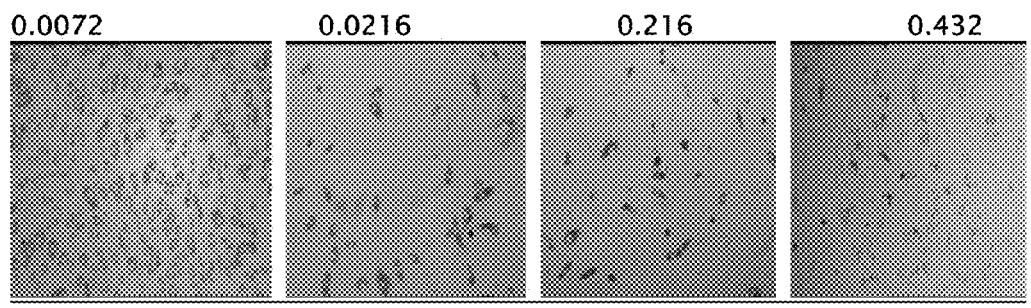
0.0072    0.0216    0.216    0.432
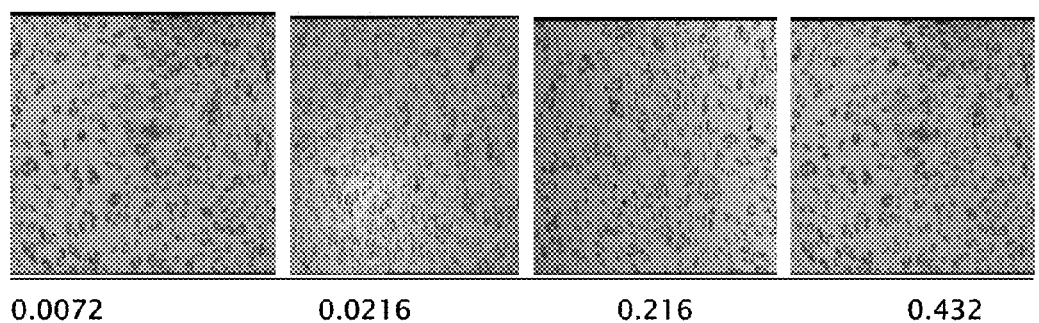
0.0072    0.0216    0.216    0.432
Row II: PC-III treated cells FIG. III
Dermal Papilla cells treated with 0.5% concentrate of liquid endosperm of *Cocos nucifera*, comprising not less than 40% w/w of total dissolved solids.
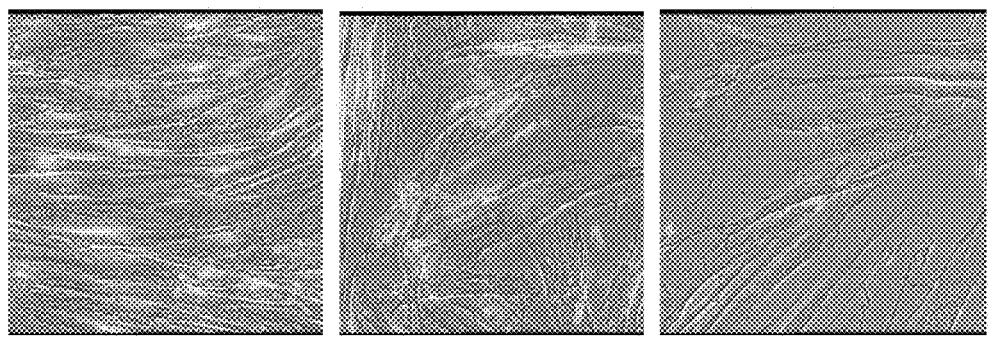
No UV exposure 0.432 J cm$^{-2}$ 0.648 J cm$^{-2}$ FIG. IV
Effect of UV on dermal papilla cells treated with PC-II at 0.648 J cm$^{-2}$
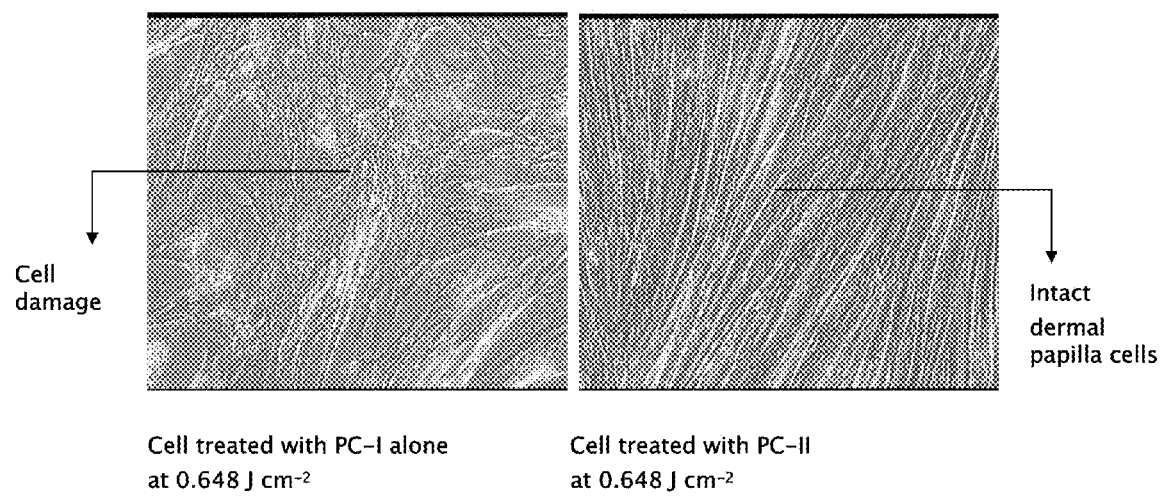
Cell damage
Intact dermal papilla cells
Cell treated with PC-I alone at 0.648 J cm$^{-2}$
Cell treated with PC-II at 0.648 J cm$^{-2}$ FIG. V
Effect of UV on dermal paplilla cells treated with PC-IV at 0.648 J cm$^{-2}$
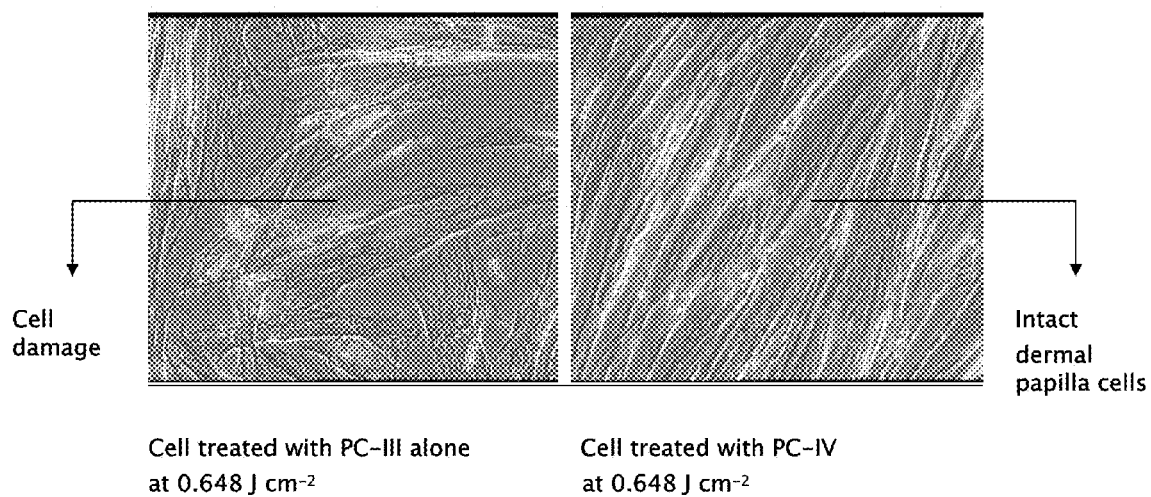
Cell damage
Cell treated with PC-III alone at 0.648 J cm$^{-2}$
Cell treated with PC-IV at 0.648 J cm$^{-2}$
Intact dermal papilla cells

PROTECTIVE COMPOSITIONS FOR DERMAL PAPILLA CELLS

BACKGROUND OF THE INVENTION

1. Field of the Invention

The invention in general relates to hair care compositions. More specifically, the protective compositions of the present invention include β-glucogallin, gallates and concentrate of liquid endosperm of *Cocos nucifera*.

2. Description of Prior Art

The maintenance of key cytological features and healthy survival of dermal papillary cells in considerable numbers is essential for the growth of hair and associated gland systems of the skin. Hair dermal papilla cells are specialized mesenchymal cells that exist in the dermal papilla located at the bottom of hair follicles. These cells play pivotal roles in hair formation, growth, and cycling. Dermal papilla cells accumulate below undifferentiated epidermis which is then stimulated to grow down into the dermis as a hair "peg". Interaction between the hair peg and the dermal papilla cells promotes differentiation into a mature hair follicle. Some important references on hair follicle development include:

1. Paus R, Muller-Rover S, Van Der Veen C, Maurer M, Eichmuller S, Ling G, Hofmann U, Foitzik K, Mecklenburg L, Handjiski B. A comprehensive guide for the recognition and classification of distinct stages of hair follicle morphogenesis. J Invest Dermatol. 1999 October; 113 (4): 523-32;
2. McElwee K J, Hoffmann R. Growth factors in early hair follicle morphogenesis. Eur J Dermatol. 2000 July-August; 10 (5):341-50.
3. Holbrook K A, Minami S I. Hair follicle embryogenesis in the human. Characterization of events in vivo and in vitro. Ann N Y Acad Sci. 1991 Dec. 26; 642:167-96.
4. Pinkus H. Embryology of hair. In: The biology of hair growth. Montagna W, Ellis R A (eds). Academic Press Inc, New York, 1958, pp 1-32.
5. Chase H B. Growth of the hair. Physiol Revs. 1954; 34:113-126.
6. Fraser D A. The development of the skin of the back of the albino rat until the eruption of the first hairs. Anat Rec. 1928; 38:203-223
7. Koelliker A. Zur Entwicklungsgeschichte der äusseren haut. Zwiss Zool. 1850; 2:67-92.

It is the principle objective of the present invention to disclose the ability of protective compositions comprising β-glucogallin, gallates and concentrate of liquid endosperm of *Cocos nucifera* to protect the dermal papilla cells from stress signals, more specifically UV rays.

The present fulfills the aforesaid objectives and provides further related advantages.

SUMMARY OF THE INVENTION

The present invention discloses novel protective compositions for dermal papilla cells. In one embodiment the said protective compositions comprise 0.25% w/w or greater of compositions including at least 10% w/w or above of 1-O-galloyl-β-D-glucose (β-glucogallin) represented by STR#1. In an embodiment, the said protective composition additionally comprises 50% to greater than 50% total gallates including mucic acid 1,4-lactone 5-O-gallate represented by STR#2, mucic acid 2-O-gallate represented by STR#3, mucic acid 6-Methyl ester 2-O-gallate represented by STR#4, mucic acid 1-Methyl ester 2-O-gallate represented by STR#5 and ellagic acid represented by STR#6. In another embodiment the invention also encompasses synergistic protective compositions for dermal papilla comprising 0.25% w/w or above of compositions comprising I. At least 10% w/w or greater of 1-O-galloyl-β-D-glucose (β-glucogallin) represented by STR#1 and 0.5% concentrate of liquid endosperm of *Cocos nucifera*, said concentrate including at least 40% total dissolved solids;

II. At least 10% w/w or greater of 1-O-galloyl-β-D-glucose (β-glucogallin) represented by STR#1 along with 50% to greater than 50% total gallates including mucic acid 1,4-lactone 5-O-gallate represented by STR#2, mucic acid 2-O-gallate represented by STR#3, mucic acid 6-Methyl ester 2-O-gallate represented by STR#4, mucic acid 1-Methyl ester 2-O-gallate represented by STR#5 and ellagic acid represented by STR#6; and 0.5% concentrate of liquid endosperm of *Cocos nucifera*, said concentrate including at least 40% w/w total dissolved solids.

The aforesaid synergistic compositions are unique in that the extracts from the endosperm of *Cocos nucifera* as such are not protective to dermal papilla cells from stress signals such as UV, as it could not prevent the cell damage due to exposure to increasing UV dosages. However, when applied along with protective composition PC-I comprising at least 10% w/w of 1-O-galloyl-β-D-glucose (β-glucogallin) represented by STR#1 or along with protective composition PC-III comprising at least 10% w/w of 1-O-galloyl-β-D-glucose (β-glucogallin) represented by STR#1 and 50% to greater than 50% gallates including mucic acid 1,4-lactone 5-O-gallate represented by STR#2, mucic acid 2-O-gallate represented by STR#3, mucic acid 6-Methyl ester 2-O-gallate represented by STR#4, mucic acid 1-Methyl ester 2-O-gallate represented by STR#5 and ellagic acid represented by STR#6, it increases the tolerance of dermal papilla cells to stress stimuli such as increasing UV dosages, while maintaining sufficient cell numbers also. Precisely, the UV protection factor attained by PC-I and PC-III for dermal papilla cells was 20. However, PC-I and PC-III when applied in combination with extracts from the endosperm of *Cocos nucifera*, the UV protection factor attained was 30. Thus the synergistic compositions are directed towards helping the dermal papilla cells to form sufficient numbers and to retain a healthy morphology conducive for hair growth.

Other features and advantages of the present invention will become apparent from the following more detailed description, taken in conjunction with the accompanying drawings, which illustrate, by way of example, the principle of the invention.

BRIEF DESCRIPTION OF THE DRAWINGS

FIG. I shows photomicrographs of the ability of the protective composition PC-I to protect the dermal papilla cells from the UV stress signal at different dosage levels.

FIG. II shows photomicrographs of the ability of the protective composition PC-III to protect the dermal papilla cells from the UV stress signal at different dosage levels.

Figure 1:
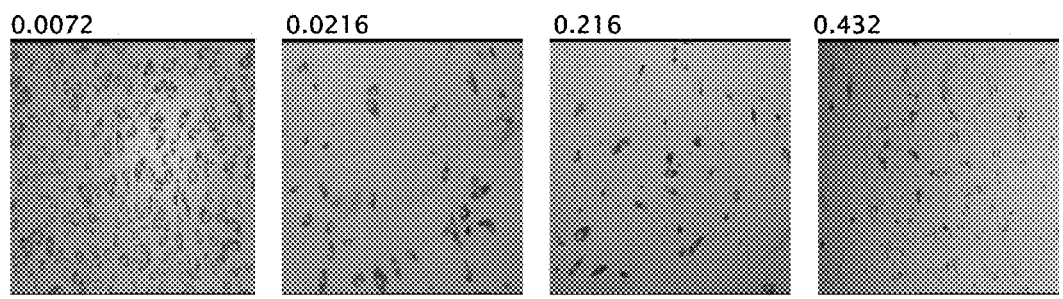
Figure 1:
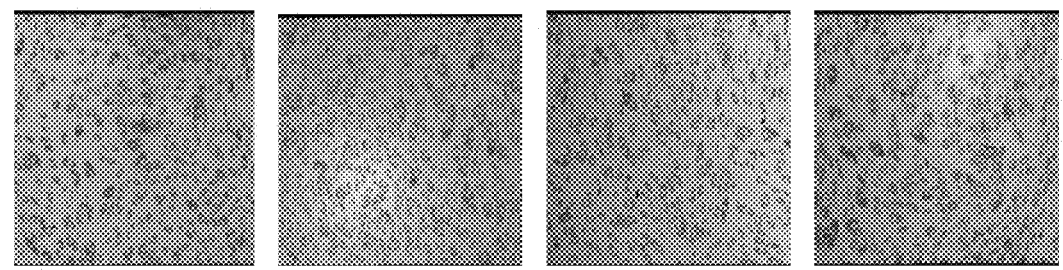

FIG. III shows the photomicrographs of 0.5% concentrate of liquid endosperm of *Cocos nucifera*, said concentrate comprising not less than 40% w/w of total dissolved solids unable to protect dermal papilla cells singly.

FIG. IV shows photomicrographs of the ability of the protective composition PC-II to improve the tolerance of dermal papilla cells to even higher UV dosages.

FIG. V shows photomicrographs of the ability of the protective composition PC-IV to improve the tolerance of dermal papilla cells to even higher UV dosages.

DETAILED DESCRIPTION OF THE MOST PREFERRED EMBODIMENT

FIGS. I to V

In the most preferred embodiment, the present invention relates to protective composition I (PC-I) comprising 0.25% w/w or above of the composition comprising at least 10% w/w or above of 1-O-galloyl-β-D-glucose (β-glucogallin) represented by STR#1. In another most preferred embodiment, the present invention relates to synergistic protective composition (PC-II) comprising PC-I along with 0.5% concentrate of liquid endosperm of *Cocos nucifera*, said concentrate comprising not less than 40% w/w of total dissolved solids. In yet another most preferred embodiment, the present invention also includes protective composition (PC-III) which comprises 0.25% w/w or above of the composition comprising at least 10% w/w or above of 1-O-galloyl-β-D-glucose (β-glucogallin) represented by STR#1 along with 50% or greater of other gallates including mucic acid 1,4-lactone 5-O-gallate represented by STR#2, mucic acid 2-O-gallate represented by STR#3, mucic acid 6-Methyl ester 2-O-gallate represented by STR#4, mucic acid 1-Methyl ester 2-O-gallate represented by STR#5 and ellagic acid represented by STR#6. In yet another most preferred embodiment, the invention includes synergistic protective composition (PC-IV) that includes PC-III along with 0.5% w/w concentrate of liquid endosperm of *Cocos nucifera*, said concentrate comprising not less than 40% w/w of total dissolved solids. The aforesaid protective compositions PC-I, PC-II, PC-III and PC-IV protect dermal papilla cells from stress signals, in specific Ultraviolet rays B (UVB). As alternative embodiments, the stress signals also include chemicals such as ferrous sulphate and inflammation mediators of immunological origin like TNF-α.

[STR#1]

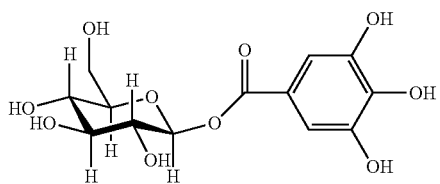

[STR#2]

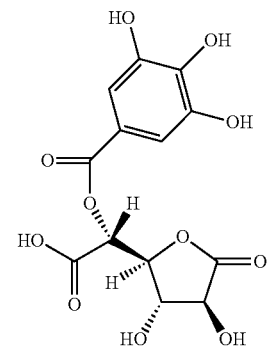

[STR#3]

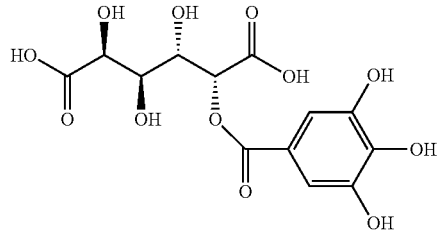

[STR#4]

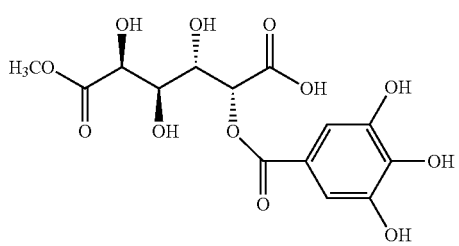

[STR#5]

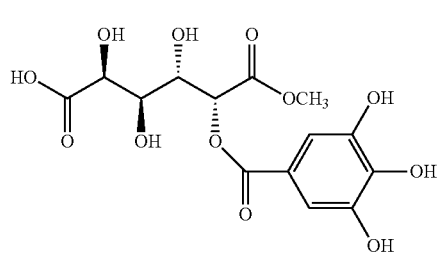

[STR#6]

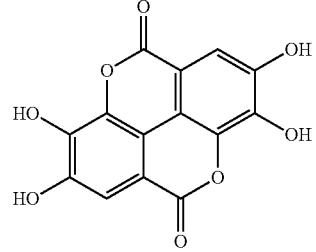

To further elucidate the most preferred embodiments of the present invention, the following examples are included herewith.

Example I

FIGS. I and II

Protection of Dermal Papilla Cells from Increasing Dosage Levels of UVB.

The cell viability of human dermal papilla after UV exposure is analyzed by Neutral Red Uptake (NRU) assay. The absorbance due to the viable cells is read at 492 nm in a Micro plate reader. The cell viability is measured after treatment with PC-I and PC-III.

Human dermal papilla cells were plated in a 96 well flat bottom clear micro plate at a seeding density of 5000 cells per well. The 24 hr monolayer of cells was exposed to increasing UV dosages in the range 0.0072 to 0.648 J cm−2, with and without sample treatment. After exposure, the cells were incubated in a CO2 incubator for 48 hrs and developed by the NRU staining techniques to analyze the cell viability.

Both PC-I and PC-III were able to protect the human dermal papilla cells from higher UVB exposure of 0.43 J cm−2.

Without sample treatment, the UVB was cytotoxic at dosage of 0.0216 J cm−2. Hence, the UV protection factor, the ratio of cytotoxic dosage for treated cells to that of the untreated cells is 20.

Example II

UV Protection effect of 0.5% concentrate of the liquid endosperm of *Cocos nucifera*, said concentrate comprising not less than 40% w/w of total dissolved solids on human dermal papilla cells [FIG. III]

FIG. III clearly shows that 0.5% concentrate of the liquid endosperm of *Cocos nucifera*, said concentrate comprising not less than 40% total dissolved solids, confers no protection to human dermal papilla cells.

Example III

Effect of UV on dermal papilla cells treated with PC-II and PC-IV at 0.648 J cm$^{-2}$ (FIGS. IV and V).

FIGS. IV and V clearly show that PC-II and PC-IV clearly are able to induce tolerance of dermal papilla cells to dosages of UV up to 0.648 J cm$^{-2}$. Without sample treatment, the UVB was cytotoxic at dosage of 0.0216 J cm−2. Hence, the UV protection factor, the ratio of cytotoxic dosage for treated cells to that of the untreated cells is 30.

While the invention has been described with reference to a preferred embodiment, it will be understood by those skilled in the art that the invention that the invention is capable of other and different embodiments without departing from the invention. Hence the drawings, embodiments and description are to be regarded as illustrative and not as restrictive. Rather, the scope of the invention is to be interpreted only in conjunction with the appended claims.

Example IV

Formulations

Hair care formulation comprising 1-O-galloyl-β-D-glucose (β-glucogallin) and concentrate from the liquid endosperm of *Cocos nucifera*.

HAIR CARE FORMULATION I

| S. No. | Formula | Content % w/w |
|---|---|---|
| 1 | 10% w/w to 50% w/w of 1-O-galloyl-β-D-glucose | 0.1-1 |
| 2 | Concentrate from the liquid endosperm of *Cocos nucifera* | 0.5 |
| 2 | Tetra sodium EDTA | 0.10 |
| 3 | Arlacel 165 | 0.50 |
| 4 | Cetostearyl alcohol | 3.75 |
| 5 | Natrosol 250HHR | 0.50 |
| 6 | Incroquat CTC 30 | 3.00 |
| 7 | N-hance 3215 | 0.50 |
| 8 | Kathon CG | 0.30 |
| 9 | DC 939 Emulsion | 2.00 |
| 10 | Demineralised water | 87.85-88.75 |
| | | 100.00 |

Hair care formulation comprising 1-O-galloyl-β-D-glucose (β-glucogallin) along with gallates including mucic acid 1,4-lactone 5-O-gallate, mucic acid 2-O-gallate, mucic acid 6-Methyl ester 2-O-gallate, mucic acid 1-Methyl ester 2-O-gallate, ellagic acid and concentrate from the liquid endosperm of *Cocos nucifera*.

HAIR CARE FORMULATION II

| S. No. | Formula | Content % w/w |
|---|---|---|
| 1 | 10% w/w to 50% w/w of 1-O-galloyl-β-D-glucose along with 50% gallates including mucic acid 1,4-lactone 5-O-gallate, mucic acid 2-O-gallate, mucic acid 6-Methyl ester 2-O-gallate, mucic acid 1-Methyl ester 2-O-gallate, ellagic acid | 0.1-1 |
| 2 | Concentrate from the liquid endosperm of *Cocos nucifera* | 0.5 |
| 2 | Tetra sodium EDTA | 0.10 |
| 3 | Arlacel 165 | 0.50 |
| 4 | Cetostearyl alcohol | 3.75 |
| 5 | Natrosol 250HHR | 0.50 |
| 6 | Incroquat CTC 30 | 3.00 |
| 7 | N-hance 3215 | 0.50 |
| 8 | Kathon CG | 0.30 |
| 9 | DC 939 Emulsion | 2.00 |
| 10 | Demineralised water | 87.85-88.75 |
| | | 100.00 |

We claim:

1. A dermal papilla protective formulation comprising 0.1% w/w to 1% w/w of a synergistic composition comprising at least 10% w/w of 1-O-galloyl-β-D-glucose (β-glucogallin) represented by STR#1 and 0.5% w/w of a concentrate from the liquid endosperm of *Cocos nucifera*, said concentrate comprising not less than 40% w/w of total dissolved solids

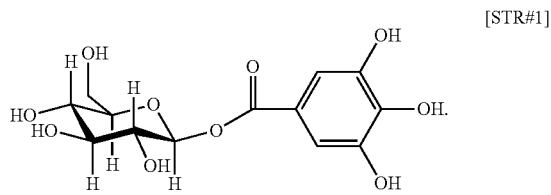

[STR#1]

2. A dermal papilla protective formulation comprising 0.1% w/w to 1% w/w of a synergistic composition comprising a. at least 10% w/w of 1-O-galloyl-β-D-glucose (β-glucogallin) represented by STR#1, 50% to greater than 50% gallates including mucic acid 1,4-lactone 5-O-gallate represented by STR#2, mucic acid 2-O-gallate represented by STR#3, mucic acid 6-Methyl ester 2-O-gallate represented by STR#4, mucic acid 1-Methyl ester 2-O-gallate represented by STR#5 and ellagic acid represented by STR#6; and b. 0.5% w/w of the concentrate from the liquid endosperm of *Cocos nucifera*, said concentrate comprising not less that 40% w/w of total dissolved solids

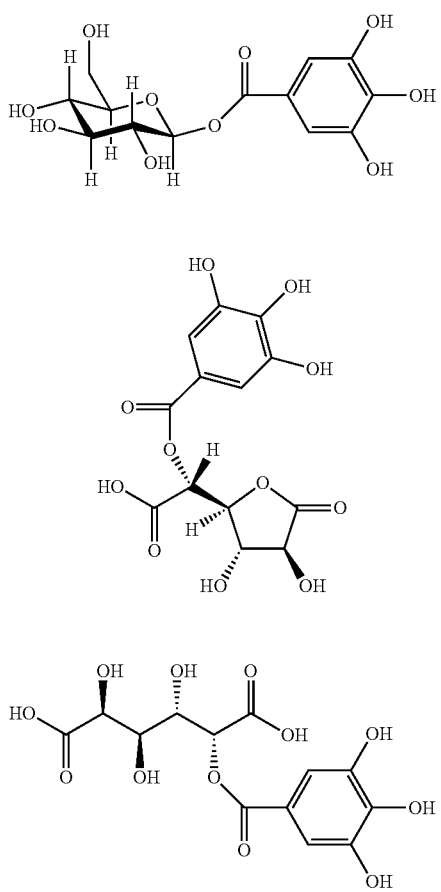
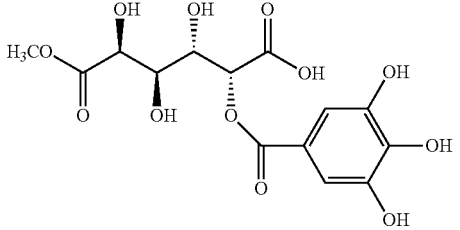
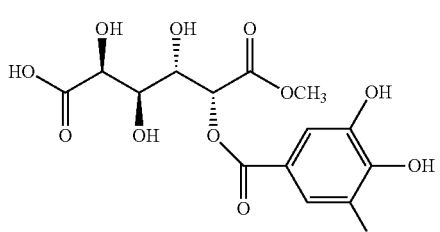
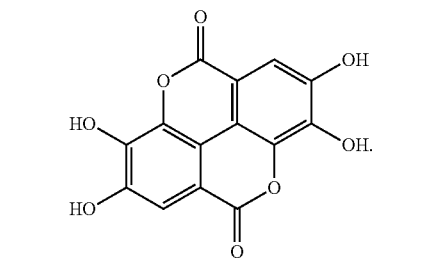
3. A method of promoting the increased tolerance of dermal papilla cells to stress signals, said method comprising step of bringing into contact dermal papilla cells and the protective formulation as claimed in claim 1 or 2.
* * * * *